(12) United States Patent
Limontini

(10) Patent No.: US 9,668,905 B2
(45) Date of Patent: Jun. 6, 2017

(54) CONFORMABLE CERVICAL COLLAR

(71) Applicant: Flavio Limontini, San Pietro Mosezzo (IT)

(72) Inventor: Flavio Limontini, San Pietro Mosezzo (IT)

(*) Notice: Subject to any disclaimer, the term of this patent is extended or adjusted under 35 U.S.C. 154(b) by 588 days.

(21) Appl. No.: 14/047,408

(22) Filed: Oct. 7, 2013

(65) Prior Publication Data
US 2014/0296758 A1    Oct. 2, 2014

(30) Foreign Application Priority Data

Mar. 26, 2013  (IT) .............................. MI20130109 U

(51) Int. Cl.
*A61F 5/055* (2006.01)

(52) U.S. Cl.
CPC .................................... *A61F 5/055* (2013.01)

(58) Field of Classification Search
CPC ....................................................... A61F 5/055
See application file for complete search history.

(56) References Cited

U.S. PATENT DOCUMENTS

| | | | |
|---|---|---|---|
| 3,374,785 A * | 3/1968 | Gaylord, Jr. ............ | A61F 5/055 602/18 |
| 3,916,884 A * | 11/1975 | Attenburrow ............ | A61F 5/01 128/DIG. 23 |
| 3,943,923 A | 3/1976 | Scheinberg | |
| 3,964,474 A * | 6/1976 | Fox ......................... | A61F 5/055 128/DIG. 23 |
| 4,232,663 A * | 11/1980 | Newton .................. | A61F 5/055 128/DIG. 23 |
| 4,676,233 A * | 6/1987 | Scheinberg ............. | A61F 5/055 128/DIG. 23 |
| 4,987,891 A * | 1/1991 | Gaylord, Jr. ............ | A61F 5/055 128/DIG. 23 |
| 5,060,661 A | 10/1991 | Howard | |
| 5,275,581 A * | 1/1994 | Bender .................... | A61F 5/055 128/DIG. 23 |
| RE35,290 E | 7/1996 | Druskoczi | |
| 5,785,670 A * | 7/1998 | Hiebert .................... | A61F 5/055 128/DIG. 23 |
| 5,788,658 A * | 8/1998 | Islava ...................... | A61F 5/055 602/18 |
| 6,458,090 B1 * | 10/2002 | Walpin .................... | A61F 5/055 128/DIG. 23 |
| 8,449,485 B2 | 5/2013 | Modglin | |

* cited by examiner

*Primary Examiner* — Tarla Patel
(74) *Attorney, Agent, or Firm* — Joseph H. Taddeo

(57) ABSTRACT

A neck collar with a first shaped condition adequate for application to the patient's neck, mold and conform to the patient's neck configuration, retain and recall that configuration following removal and reapplication to the patient. A second shaped condition for storage. The collar is achieved by a unique piece of conformable material that is sufficiently resilient to maintain the given shape. The main body is designed to provide support and recall the anatomic shape of a particular patient's cervical spine.

35 Claims, 4 Drawing Sheets

CONFORMABLE CERVICAL COLLAR

CROSS REFERENCE TO RELATED APPLICATIONS

This application claims the benefit of Utility Model Application number MI2013U000109, filed Mar. 26, 2013, with the Chamber of Commerce, Industry, Craft and Agriculture of Milan, IT, by the present inventor, Flavio Limontini, CEO of FLAMOR, s.r.l., with headquarters located at NOVARA (NO), VIA BIANDRATE 80, 28060 SAN PIETRO, ITALY, which application is incorporated herein by reference.

FIELD OF THE INVENTION AND BACKGROUND

The invention relates to a stabilizing neck collar for fixation of the cervical vertebrae and more particularly to a conformable cervical collar with an ergonomic design that patterns itself to a patient's neck.

Adjustable neck braces in the prior art include inflatable head and neck supports. Other devices for the same purpose are provided with panels that are connected by means of positioning grooves and have adjustment knobs. Other cervical devices include one or more opposing arms for folding between a flat and an upright position for engagement by a locking device.

Still other cervical collar devices have a shell with front and back members and means to adjustably join the members using a plurality of elongated slits.

Review of these disclosures indicates that what is needed is a conformable cervical collar that is easy to use. The requirement is for a neck brace that can be applied to a patient with minimal displacement of the neck and reduced disarticulation of the cervical vertebrae.

Moreover, there is a need for a brace which can initially be molded to a patient's neck. And then, having sufficient resilience following removal of the brace for rehabilitation requirements, sleeping or bathing, the resilient brace retains its prior form for reapplication to restore cervical support to the same patient without further adjustments.

DESCRIPTION OF THE PRIOR ART

The following prior art discloses the various aspects in the design and use of adjustable cervical collars.

The patent for a SPLINT AND METHOD OF APPLYING SAME, U.S. Pat. No. 3,943,923, granted to Samuel Scheinberg, Mar. 16, 1976, discloses a splint comprising an elongated rectangular flat strip of malleable metal that is rollable and foldable into a compact package for storage or shipment.

U.S. Pat. No. 4,676,233, for MANUALLY FORMED SPLINTS HAVING SHEET METAL STRUCTURE, was issued to Samuel Scheinberg, Jun. 30, 1987, provides a splint of thin malleable sheet metal, preferably dead soft aluminum, wherein a stiffening flange or rib that extends longitudinally and centrally along the material to support the body member on which the splint is used.

Applicant's cites U.S. Pat. No. 5,060,661, to Thomas L. Howard, dated Oct. 19, 1991, titled INFLATABLE NECK AND HEAD SUPPORT, which features an inflatable closed chamber for encompassing the neck and supporting the head of the wearer.

A patent for a SURGICAL COLLAR AND LINER THEREFOR, Pat. No. Re. 35,290, was granted to Sue Druskoczi, on Jul. 2, 1996, which discloses a liner formed of a blank of soft pliable material conformed to the interior surface of a surgical collar.

U.S. Pat. No. 8,449,485, issued to Michael D. Modglin, May 28, 2013, discloses a CERVICAL COLLAR WITH CABLE REEL ADJUSTMENT SYSTEM.

SUMMARY OF THE INVENTION

The object of the invention is a cervical collar and, in particular, a rigid cervical collar, meant to be used in EMS operations to prevent any unintended movement of the neck, such as bending, extension or rotation. Collars of this type are useful to avoid any potential damage to the cervical vertebrae which could involve permanent lesions or paralysis, and possibly even the death of the patient as a consequence of the damage to the spinal cord.

A cervical collar as disclosed here is designed for EMS operations. The device generally includes a body of flexible plastic material, for example polyethylene, coated with expanded closed foam, such as for example EVA or similar materials. The body of the collar includes panels that are duly shaped to offer neck support. While lower collar portions are supported by the shoulders and breastbone, the chin, jaw and head are propped up by upper collar edges.

This collar presents an initial flat condition that includes closure structures on the extremities, such as for example Velcro™ strips or the like. When fitting the device on the patient, the collar is duly applied behind the nape, thereafter bent in order to wrap completely around the patient's neck and fastened using the closures provided. After removal from the patient's neck, the collar can be restored to its original shape and can be stored for a next use.

One of the major problems of prior art cervical collars pertains to their bulk. In fact, when prior art collars are in an original flat shape, a total length can exceed 60 cm, (23.6 inches). Since such collars are often included in the standard equipment of an EMS backpack, for example during military operations in the field or during EMS actions performed by rescue teams in disaster area, reductions in length, width and bulk are desirable.

Another problem with prior art cervical collars relates to their complexity in application and use. For example, certain cervical collar models on the market lack a movable chin support that would make it adaptable to the patient's weight, size, configurations and proportions. Once the collar has been positioned, the chin support is moved to an advantageous position and its movement is obstructed by lack of sufficient means to maintain the desired jaw and chin position. It is therefore evident that the application of such prior art collars is overly complex, slow and potentially dangerous, giving primary consideration to the fact that such operations are often performed in unfavorable conditions where the time factor may be critical to saving the patient.

The device for immobilization of fractured limbs shown in U.S. Pat. No. 4,676,233, an "immobilization splint", is made by a strip of shapeable material which could supply the necessary stiffness once duly folded in order to form fitting reinforcing ribs. This patent also describes developing a neck collar by duly shaping the malleable material. However, it is impossible to adapt this product to the shape of the neck and chin of the patient to obtain a correct and effective immobilization. The several folded areas, stiffening posts or flanges of the '233 patent, which the patent requires to form the ribs for rigidity along the circumference of the neck, render the device ineffective as well as slow, complex and cumbersome to apply.

Thus, a primary object of the present invention is to provide an improved neck collar which is easy to apply and adjust to contours of a patient's neck.

Another object of the present invention is delivery of a neck collar comprising a single piece.

Yet another object of the present invention is to afford a neck collar which is light-weight, less bulky and easy to transport.

A still further objective of the present invention is the provision of a supple neck collar that molds to a patient's neck and chin having sufficient resilience to maintain its conforming shape after removal for later reapplication to the same patient.

Another object is formation of the collar main body using a core sheet of aluminum or its alloys surrounded by an outer coating of an expandable material, for example a polyurethane closed cell foam.

An added objective is to provide a neck collar opening in the throat area to allow access for a tracheotomy although the collar has already been applied to the patient.

Still a further goal is formation of a second opening in the body portion of the collar to allow ventilation at the nape of the neck.

One more object is the formation of a chin adapter with upstanding pegs which can rotate toward and away from the neck for chin support and comfort.

These and other objectives are achieved by the present invention as disclosed and claimed herein. Further characteristics and advantages of the invention are described below and defined in the claims.

The neck collar of the invention includes at least a first shape or condition suitable for application to the neck of a patient to prevent movement of the cervical vertebrae. The collar is advantageously realized with a unique piece made by a shapeable material that retains a given molded shape. And the main body is designed to present on the front side at least a partial support for the patient's chin. In a second shaped condition, the neck collar is transformed by rolling up the main body of the collar or, in the alternative, folding the main body one or more times to a minimal size that facilitates shipment and storage.

The designation "shapeable material" means here and subsequently, a material which can be manually misshaped, which is able to keep the determined shape, and which can be later transformed manually, to its original shape.

A collar according to the invention can easily be unfolded to a condition ready for use. The collar design enhances simplicity in application to a patient's neck. Thus, the neck collar according to the invention can easily be unfolded and shaped in a condition ready for use. The predetermined shape gives the collar a particular easiness in applying the collar to the patient's neck. The neck collar is just as easy to store due to the adaptability for folding the material in the most appropriate shape, rolled or folded, to occupy the smallest space.

The material for the main body includes for example an internal foil of aluminum or its alloys and an external coating is fabricated for example with a closed cell foam. The aluminum alloy foil facilitates folding as well as maintenance of the conforming shape while the outside coating of foam, further than being a protection coating, provides comfort for the patient.

According to another advantageous aspect of the invention, the section for chin support includes several small wings adjusting the collar to the shape of the face and neck of the patient. Therefore, adapting the collar to a patient is quick and easy.

In any case, to guarantee safety of the collar after its application, a means for repositionable closing is provided such as, for example, a system of bands retained together by opposing hooks and loops.

BRIEF DESCRIPTION OF THE DRAWINGS

Further characteristics and advantages of the present invention will result more evident from the following description, realized as an example, with reference to the attached drawings, wherein.

Drawing

Drawing

DETAILED DESCRIPTION OF THE INVENTION

Figure 1:
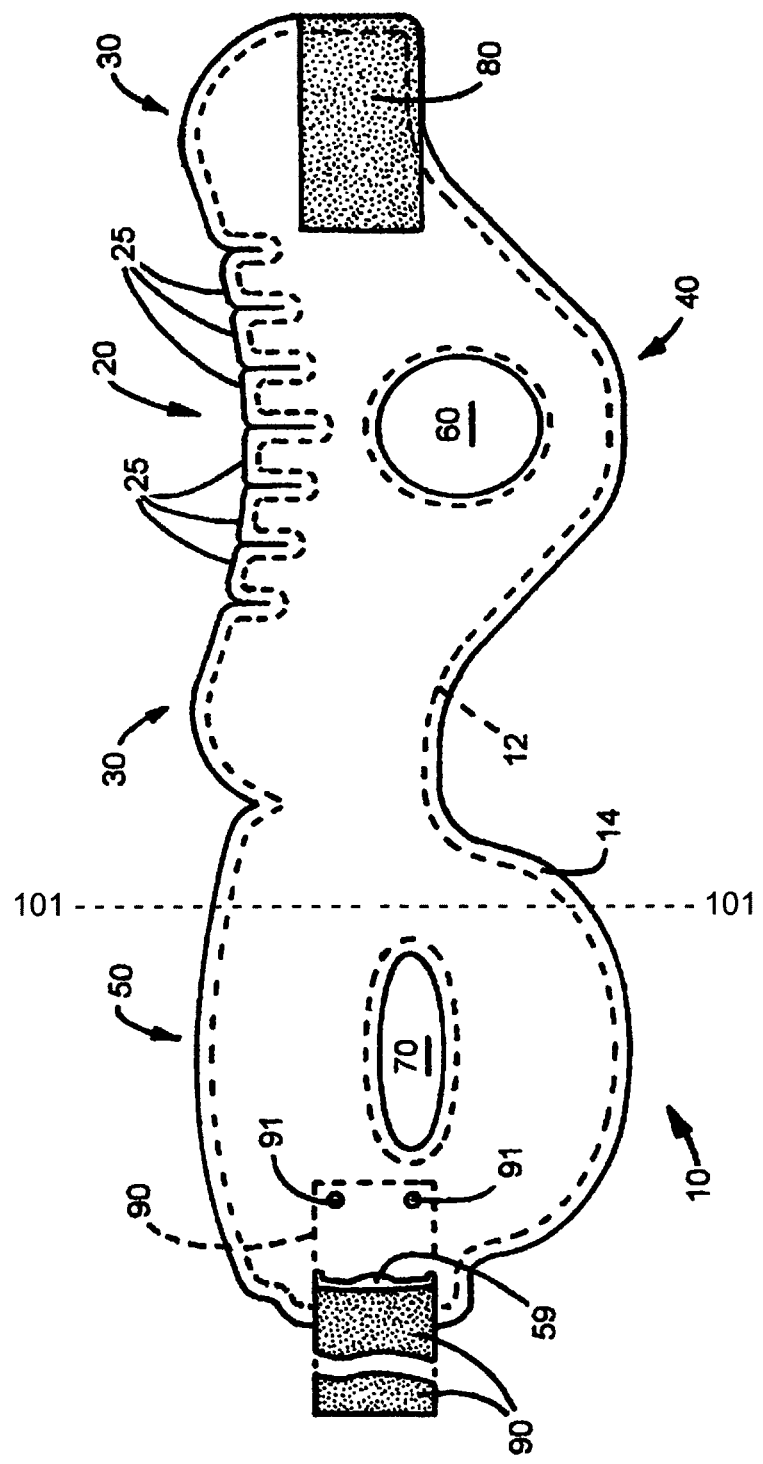
FIG. 1 is an elevation view showing the neck collar in an open condition according to its preferred shape of the invention.

Drawing FIG. 1 illustrates a neck collar 10 from an external elevation view. The broken line displays the edges of an internal core comprising a smooth pliable sheet material such as, inter alia, an aluminum foil 12, while the edging with full stroke line indicated the coating 14, constructed of an elastic material, such as for example a polyurethane foam, an expanded elastomer, Ethylene Vinyl Acetate foam, (EVA), or similar foam thermoplastic elastomers capable of functioning as an energy absorbing or padding material. The foil core 12 and the coating 14 are congruent and make a unique single planar piece which constitutes the main body of the neck collar 10 forming a functionally shaped support panel element. The core 12 can have for example a thickness of approx. 0.5 mm, (0.01968 in), but it can also be realized with thicknesses between 0.3 mm and 0.8 mm, (0.01181 in. to 0.03149 in.); lower ranges of thickness fail to provide a requisite collar stiffness, while higher thicknesses increase difficulty in shaping the collar. Aluminum behaves elastically under loading conditions with the ability to resume both shape and size, a preferred characteristic when flexible strength is required. The foil thickness is critical to preserve the core's energy absorption when deformed elastically wherein the cervical collar is conformed around a patient's neck by a mild hand pressure without the need for special tools or any other intervention, and to return it when unloaded in a resilient recall of the formed shape. Resilience is measured by the modulus of resilience, which is the strain energy per unit volume required to stress the material from zero stress to the yield stress. The ability to withstand such stress without fracturing is particularly desirable in medical devices, namely in this case cervical collars.

A laminate layer of padding forms a coating 14, which is essentially co-extensive with the foil core 12. Since thickness of the laminate coating 14 affects bulk of the collar, the coating is generally set so that the collar can have a total thickness included between 4 mm and 8 mm, (0.1574 in. to 0.3149 in.), for example a thickness of approx. 5 mm, (0.1968 in.). In any case it is better to establish a noticeable thickness on the edges and on the internal side, so the parts which are directly in contact with the patient are thicker, while the coating thickness on the external surface is reduced.

The main body of the neck collar 10 is shaped as a single planar member that is defined to form different functional support parts or plates adapted to patient structures contacted by the collar 10; in particular a plate 20 for the support of the chin which is flanked by two plates 30 for supporting the lower jaw, a part or plate 40 for anchoring the collar 10 against the breastbone and a part 50 for backing at the nape.

Between plates 20 and 40 of the collar 10 there is an opening 60 in order to allow to the EMS staff to practice any tracheotomy even when the collar has already been applied to the patient. A second opening 70 is realized in the part 50 of the body of the collar 10 in order to favor the nape's ventilation.

The collar 10 is moreover equipped with a repositionable closing device, such as a device with a system matching opposite bands of loops and hooks of Velcro® or similar devices. The closing device presented here includes in this case a plate 80 equipped with hooks which is fixed, for example by gluing it, to the external side of the body of the collar 10, to the extremity which is positioned corresponding to one of the parts 30 supporting the lower jaw. At the opposite side there is opposed a band 90 equipped with loops and fixed to the internal side of the body of the collar 10 by means of rivets 91 or similar fixing devices; the band comes outside the body of the collar 10 through a slot 59 and has a length which is duly chosen to adapt the collar 10 to the several sizes for which it is intended.

Figure 2:
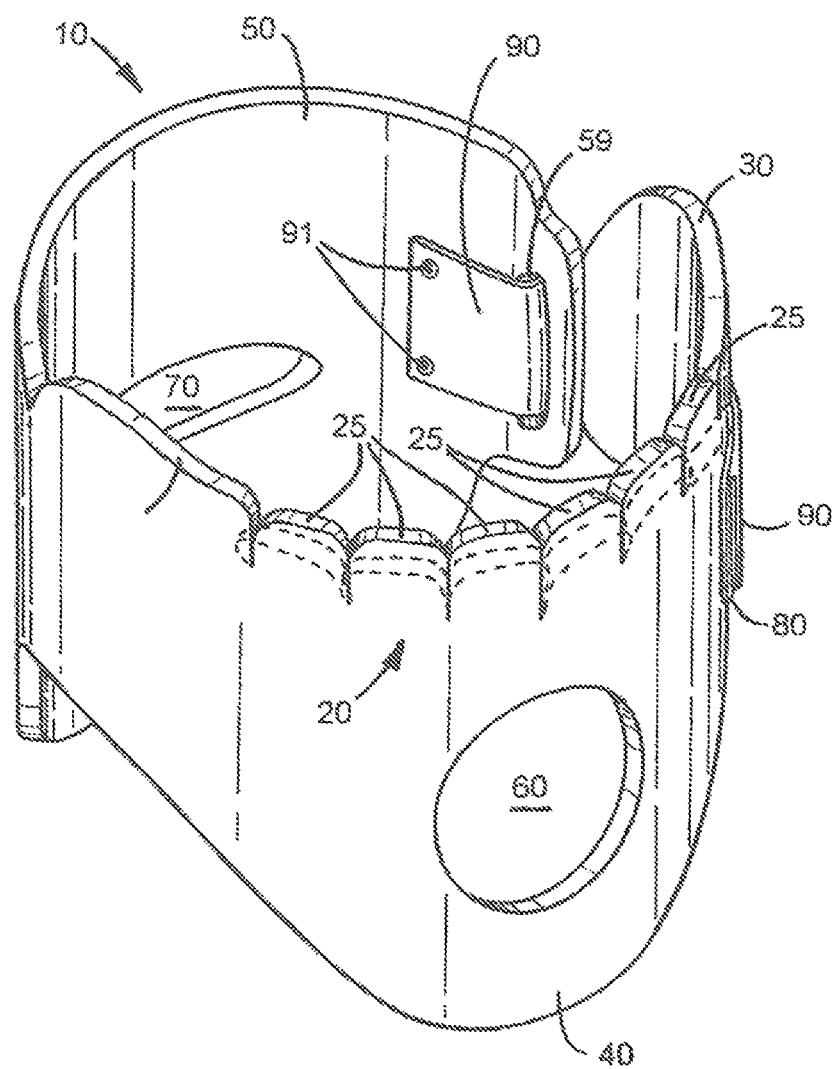
FIG. 2 is an elevation view of the neck collar of Drawing FIG. 1 shown in formation for use in application to the neck of a patient; and Drawing

Drawing FIG. 2 illustrates the neck collar 10 of Drawing FIG. 1 in an open, planar condition, i.e. the one assumed when it is applied to the patient's neck. It is notable that the section 20 comprises a chin adapter for supporting the chin and includes several repositioning upright wings or pegs 25 allowing quick and easy adaptation of the collar to the shape of the patient's jaw and chin. The wings 25, represented in FIG. 2 with full stroke line in their own original position can be therefore moved forward or back and shaped by a simple bend or folding in order to give them the configuration represented for example with the broken line.

Figure 3:
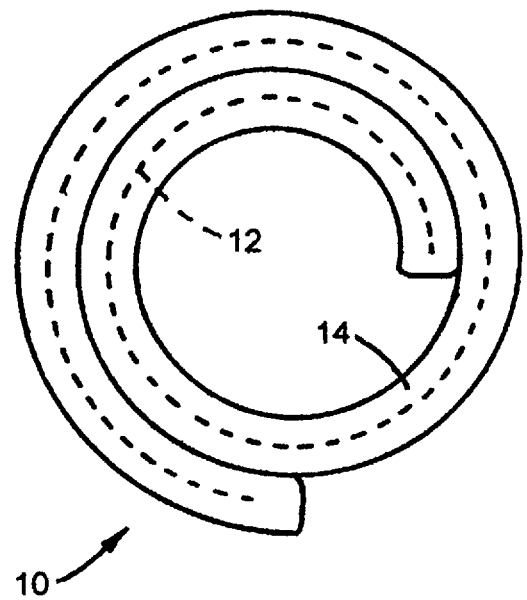
FIGS. 3 and 4 show schematic views of the shapes which the neck collar of Drawing FIG. 1 can assume in order to limit volume and allow an easier storage in limited spaces.
Figure 4:
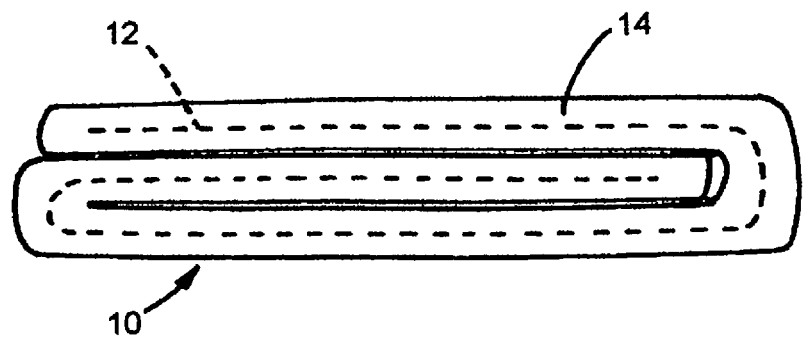

A neck collar 10 according to the invention can also be shaped in a suitable condition to be shipped or stored in a small space, for example by shaping the main body of the collar 10 in a roll (Drawing FIG. 3) or in a folded and flat condition (Drawing FIG. 3).

In summary, the particular construction characteristic of a collar 10 according to the invention makes it easy to be folded, rolled up or anyway allows to give it reduced and compact shape and dimensions, adequate for placing it inside a rescue backpack. Once applied to the neck of the patient, the collar 10 becomes rigid so that it can immobilize it steadily. A neck collar 10 according to the invention is additionally quite light, around 100 g, (3.5274 oz.), and lends itself therefore to be adopted in a transportable EMS rescue kit without having any significant impact on their total weight.

Figure 5:
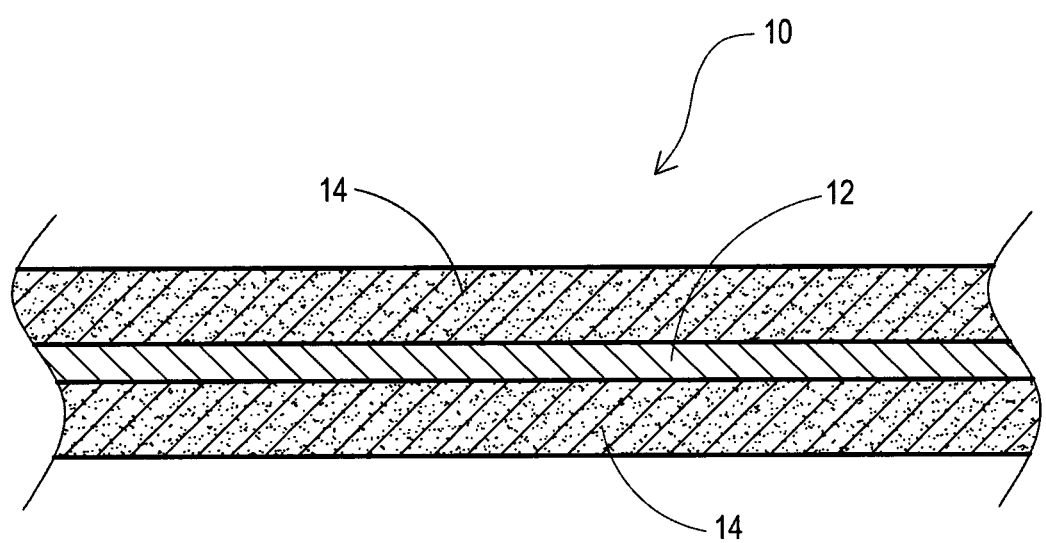
FIG. 5 is a cross-section view along line 101-101 of FIG. 1, owing the three layers of the main body of the neck collar 10.

Referring to FIG. 5, a cross-section view taken on line 101-101 of FIG. 1, there is shown the smooth pliable aluminum foil sheet 12 encased within the energy absorbing padding of a thermoplastic foam material 14.

The core can also be formed of an aluminum alloy having a proof resilience, that is, a range of maximum energy that can be absorbed within the elastic limit, without creating a permanent distortion. The core modulus of resilience is computed by the formula, $$U_r = \frac{\sigma_y^2}{2E}$$

where $U_r$ is the modulus of resilience, σy is the yield strength, and E is Young's modulus. Of course, the core disclosed here is preferably constructed of an aluminum alloy which is within the proof resilience range so that the collar is not permanently deformed when manually molded on a patient's neck.

Several modifications can be made by an expert in this field without departing from the spirit of the invention. For example, the closing device can also be different from the one which is now represented by loops and hooks. Similarly, the device can also include more than one plate of hooks 80 and even more than one strip of loops 90.

The invention claimed is:

1. A conformable cervical collar including a main body of a single piece and having a non-foam, malleable material center core surrounded by an energy absorbing material, wherein the center core is capable of being manually molded, but not permanently deformed in a configuration around a patient's neck; such that an absorbed energy of the manually molded core is restored in a resilience recall of an anatomic shape of a particular patient's cervical spine; wherein after removal, a reapplication of a collar requires no further fitting or intervention due to the resilience recall wherein the center core comprises an aluminum foil sheet that is coated on all sides with a thermoplastic elastomer, wherein the aluminum foil sheet and the thermoplastic elastomer are congruent, and wherein the thermoplastic elastomer has no ribs or flanges which may jab and irritate a patient wherein the aluminum foil sheet and the thermoplastic elastomer are congruent.

2. A conformable cervical collar as defined in claim 1, wherein the thermoplastic elastomer comprises a closed cell polyurethane.

3. A conformable cervical collar as defined in claim 2, wherein the a cervical collar is conformed around a patient's neck by a mild hand pressure without the need for special tools or any other intervention.

4. A conformable cervical collar as defined in claim 3, wherein the main body is shaped for support of selected anatomic parts of a patient, including a chin adapter which is flanked by two plates for supporting a patient's lower jaw, a plate to anchor the cervical collar against a patient's breastbone and a plate for backing to a patient's nape.

5. A conformable cervical collar as defined in claim 4, further comprising a chin adapter that includes several repositioning upright pegs which can be moved forward or back and shaped by a partial folding that allows quick and easy adaptation of the cervical collar to a shape of a patient's jaw and chin.

6. A conformable cervical collar as defined in claim 5, further comprising a first opening adjacent a patient's throat area to allow a tracheotomy in circumstances wherein the cervical collar has already been applied to the patient.

7. A conformable cervical collar as defined in claim 6, further comprising a second opening adjacent a nape of a patient's neck to enhance ventilation.

8. A conformable cervical collar as defined in claim 2, wherein the malleable material center core has a thickness in a range of 0.01181 to 0.03149 inches.

9. A conformable cervical collar as defined in claim 8, wherein the thermoplastic elastomer comprises a soft padding having a thickness in a range of 0.1574 to 0.3149 inches.

10. A conformable cervical collar as defined in claim 9, wherein the cervical collar is light and easy to carry with a weight of less than 3.53 ounces.

11. A conformable cervical collar as defined in claim 10, further comprising a repositionable closing device with matching opposed bands of hooks and loops, said repositionable closing device including a plate equipped with hooks which is fixed to an external side of a main body extremity which is positioned corresponding a chin adapter part supporting a patient's lower jaw; at an opposite side an opposed band equipped with loops is fixed to an internal side of the main body of the cervical collar; an internal band extends outside the main body of the cervical collar through a slot and has a length sufficient to adjust the cervical collar to various sizes and upon a proper adjustment to immobilize a patient's cervical vertebrae.

12. A conformable cervical collar as defined in claim 11, wherein the cervical collar can also be shaped in a suitable condition to be shipped or stored in a small space wherein the main body of the cervical collar is shaped in a roll.

13. A conformable cervical collar as defined in claim 11, wherein the cervical collar is folded in a flat condition to minimize a bulk of the cervical collar.

14. A conformable cervical collar as defined in claim 11, wherein the center core has a proof resilience range of maximum energy that can be absorbed within an elastic limit without creating a permanent distortion.

15. A conformable cervical collar as defined in claim 14, wherein a center core modulus of resilience is computed by the formula, $$U_r = \frac{\sigma_y^2}{2E}$$

where $U_r$ is the modulus of resilience, σy is the yield strength, and E is Young's modulus; wherein the center core is constructed of an aluminum alloy that is within the proof resilience range.

16. A conformable cervical collar as defined in claim 15, wherein the collar is not permanently deformed when manually molded around a patient's neck.

17. An attachable, removable and repositionable cervical collar comprising:
   a main body of a single planar member formed of a smooth pliable sheet material at a center core;
   a resilient outer energy absorbing padding material attached to and formed over said center core;
   wherein the padding material is essentially co-extensive with the center core;
   wherein said main body further forms more than one functionally shaped support panel element; and
   wherein said core is adapted to be moldable around a patient's neck such as to conform to a selected anatomical shape of a selected patient's cervical spine such as to absorbed energy when affixed to said patient and is further capable for resilience recall of said selected anatomical shape after removal and reapplication wherein the center core comprises an aluminum foil sheet that is coated on all sides with a thermoplastic elastomer, wherein the aluminum foil sheet and the thermoplastic elastomer are congruent, and wherein the thermoplastic elastomer has no ribs or flanges which may jab and irritate a patient.

18. The cervical collar as defined in claim 17, wherein smooth pliable sheet material has a core modulus of resilience with a resiliency range computed by the formula, $$U_r = \sigma y^2 / 2E$$

where $U_r$ is the modulus of resilience, σy is the yield strength, and E is Young's modulus.

19. The cervical collar as defined in claim 18, wherein said resilient outer energy absorbing elastic material comprises a closed cell foam thermoplastic elastomer.

20. The cervical collar as defined in claim 18, wherein said thermoplastic elastomer comprises a material selected from the group consisting of: polyurethane foam; and ethylene vinyl acetate foam.

21. The cervical collar as defined in claim 18, wherein said smooth pliable sheet material has a thickness in a range of 0.01181 to 0.03149 inches.

22. The cervical collar as defined in claim 21, wherein said resilient outer energy absorbing padding material has a thickness in a range of 0.1574 to 0.3149 inches.

23. The cervical collar as defined in claim 18, wherein said collar is adapted to be stored in a smaller form factor to minimize a bulk of the collar selected from the group consisting of: folded; and rolled.

24. The cervical collar as defined in claim 17, wherein said resilient outer energy absorbing elastic material comprises a closed cell foam thermoplastic elastomer.

25. The cervical collar as defined in claim 24, wherein said thermoplastic elastomer comprises a material selected from the group consisting of: polyurethane foam; and ethylene vinyl acetate foam.

26. The cervical collar as defined in claim 17, wherein said more than one functionally shaped support panel element is selected from the group consisting of: a chin adapter; a support plates for supporting a lower jaw; an anchor plate to anchor said collar against the breastbone; and a neck plate for backing to the nape.

27. The cervical collar as defined in claim 26, wherein said chin adapter further comprises several repositioning upright pegs which can be moved forward or back and shaped by a partial folding that allows quick and easy adaptation of the collar to the shape of a patient's jaw and chin.

28. The cervical collar as defined in claim 26, wherein said anchor plate further forms a first opening adjacent a patient's throat area adapted to allow a tracheotomy in circumstances wherein the collar has already been applied to the patient.

29. The cervical collar as defined in claim 26, wherein said neck plate further forms a second opening adjacent a nape of a patient's neck to enhance ventilation.

30. The cervical collar as defined in claim 17, wherein said smooth pliable sheet material has a thickness in a range of 0.01181 to 0.03149 inches.

31. The cervical collar as defined in claim 30, wherein said resilient outer energy absorbing padding material has a thickness in a range of 0.1574 to 0.3149 inches.

32. The cervical collar as defined in claim 17 having an overall weight of less than 3.53 ounces.

33. The cervical collar as defined in claim 17, further comprising a repositionable closing device with matching opposed bands of hooks and loops, said repositionable closing device including a plate equipped with hooks which is fixed, to an external side of a collar body extremity which is positioned corresponding a chin adapter part supporting a patient's lower jaw; at an opposite side an opposed band equipped with loops is fixed to an internal side of the body of the collar; an internal band extends outside the collar body through a slot and has a length sufficient to adjust the collar to various sizes and upon proper adjustment to immobilize a patient's cervical vertebrae.

34. A method for customizing a cervical collar as defined in claim 33 to a selected anatomical shape comprising the steps:
   a. folding said main body around a patient's cervical spine;
   b. providing manually moldable pressure to said main body about a patient's neck such as to reconfigure said pliable sheet material to said patient's cervical spine; and
   c. attachment of said closing device into a first closed position.

35. The method for customizing a cervical collar as defined in claim 34, further comprising removal of said cervical collar while maintaining resilience recall of said selected anatomical shape after removal and for reapplication.

\* \* \* \* \*